United States Patent [19]

Bartelt et al.

[11] Patent Number: 5,011,683

[45] Date of Patent: * Apr. 30, 1991

[54] AGGREGATION PHEROMONES OF THE DRIEDFRUIT BEETLE, *CARPOPHILUS HEMIPTERUS*

[75] Inventors: Robert J. Bartelt, East Peoria; Patrick F. Dowd, Peoria, both of Ill.

[73] Assignee: The United States of America as represented by the Secretary of Agriculture, Washington, D.C.

[ * ] Notice: The portion of the term of this patent subsequent to Apr. 16, 2008 has been disclaimed.

[21] Appl. No.: 275,863

[22] Filed: Nov. 25, 1988

[51] Int. Cl.$^5$ .................... A07N 25/00; A07N 27/00; C07C 9/00
[52] U.S. Cl. .................................. 424/84; 514/762; 514/789; 585/16
[58] Field of Search .................. 424/84; 514/789, 762; 585/16

[56] References Cited

PUBLICATIONS

Naarmon CA 98:127166n, 1983.
Philips CA 69:87241a, 1968.
J. M. Smilanick et al., "Attraction of Carpophilus Spp. (Coleoptera:Nitidulidae) to Volatile Compounds Present in Figs." J. Chem. Ecol. 4(6), 701–707 (1978).
S. R. Alm et al., "A Chemical Attractant for *Glischrochilus quadrisignatus* (Coleoptera: Nitidulidae)," J. Econ. Entomol. 78)4): 839–843 (1985).
S. R. Alm et al., "Attraction of *Glischrochilus quadrisignatus* (Coleoptera; Nitidulidae) to Semiochemicals: Butyl Acetate and Propyl Propionate," J. Econ. Entomol. 79(3): 654–658 (1986).
P. R. White et al., "Female Sex Pheromone of the Common Furniture Beetle *Anobium punctatum* (Coleoptera: Anobiidae): Extraction, Identification, and Bioassays," J. Chem. Ecol. 13(7): 1695–1706 (1987).

*Primary Examiner*—Stanley J. Friedman
*Assistant Examiner*—Russell Travers
*Attorney, Agent, or Firm*—M. Howard Silverstein; Randall E. Deck; John D. Fado

[57] ABSTRACT

A male-produced aggregation pheromone was demonstrated in *Carpophilus hemipterus* (L.) (Coleoptera: Nitidulidae) using a wind-tunnel bioassay. The attractiveness of the pheromone is greatly enhanced by volatiles from a host plant, and combinations of pheromone and food volatiles typically attract 3–10 times more beetles than either source by itself. The pheromone consists of a series of 13-, 14-, and 15-carbon unsaturated hydrocarbons, the most abundant of which is 3,5,7-trimethyl-(E,E,E,E)-2,4,6,8-decatetraene.

7 Claims, No Drawings

AGGREGATION PHEROMONES OF THE DRIEDFRUIT BEETLE, CARPOPHILUS HEMIPTERUS

BACKGROUND OF THE INVENTION

1. Field of the Invention

This invention relates to aggregation pheromones of insects, particularly the driedfruit beetle *Carpophilus hemipterus*, and the use of these pheromones in combination with host plant volatiles to aid in insect control as, for example, in pheromone-baited traps.

2. References

Throughout this application, various publications are referenced by the name of the author and date of publication within parentheses. Full citations for these references may be found at the end of the specification, listed in alphabetical order.

3. Description of the Prior Art

Insect-produced volatiles (e.g., pheromones) and host plant odors (e.g., kairomones) may facilitate location of conspecifics for mating and orientation to acceptable host plants for feeding and oviposition. It is known that in several insect species (e.g., bark beetles) pheromones and plant odors, such as monoterpenes, may act in synergy, each enhancing the attraction of the other (Borden, 1984).

*Carpophilus hemipterus* (L.) (Coleoptera: Nitidulidae) is a worldwide pest, attacking agricultural commodities such as ripe and dried fruit, corn, wheat, oats, rice, beans, nuts, peanuts, cotton seed, copra, spices, sugar, honey, and other materials (Hinton, 1945). It is also able to vector microorganisms responsible for the souring of figs (Hinton, 1945) and fungi which contaminate corn and produce mycotoxins (Wicklow et al., 1988).

Field traps have been used to monitor or control this and other nitidulid species, and much research has gone into trap baits. Smilanick et al (1978) determined that a 1:1:1 mixture of acetaldehyde, ethyl acetate, and ethanol was an effective bait for *C. hemipterus*. Alm et al. (1985, 1986) demonstrated that esters such as propyl propionate and butyl acetate were effective baits for *Glischrochilus quadrisignatus*, another economically important nitidulid. In nature, these chemicals exist in the host plant, are produced by microorganisms which have established on the plants, or both. Curiously, no pheromones have been reported for nitidulid beetles, even though attractants of this type would probably be potent trap baits or additives to presently used baits; pheromones have been reported for a large number of other beetle species.

SUMMARY OF THE INVENTION

We have now surprisingly found that a multicomponent, male-produced aggregation pheromone is secreted by *Carpophilus hemipterus* (L.). The attractiveness of the pheromone complex is greatly enhanced by volatiles from a host plant.

It is an object of this invention to describe the isolation and synthesis of the hydrocarbon components of the aggregation pheromone.

Another object of the invention is to teach an improved method of attracting insects by the combined use of aggregation pheromones and food volatiles.

Other objects and advantages of the invention will become readily apparent from the ensuing description.

DETAILED DESCRIPTION OF THE INVENTION

We have now discovered that male *C. hemipterus* beetles produce a volatile hydrocarbon mixture which is attractive to both sexes and is, therefore, termed an aggregation pheromone. The pheromone complex is especially effective when used in combination with volatiles from a food source. The isolation, identification, and synthesis of the pheromones and their biological activity in conjunction with food volatiles are described below. It is understood that host plant volatiles may be produced directly by the plant or by microorganisms, such as yeasts, which are growing on plant tissues.

The *C. hemipterus* beetles were reared on a pinto bean diet as described by Dowd (1987). The isolation of the pheromone for this species was guided by a wind-tunnel bioassay (described in detail in Example 1). Briefly, the wind tunnel usually contained 200–400 beetles of mixed sex. Bioassay tests always included two treatments, placed side by side, in the upwind end of the wind tunnel. The beetles located bait materials by flying upwind to the source of the attractive volatiles. The number of beetles landing at each bait was used as a measure of its attractiveness. Simultaneous testing of two treatments made precise comparisons possible, without having to control the numbers of beetles in the wind tunnel or their activity level too closely.

We believe the wind-tunnel bioassay to be more ecologically relevant than the more classical "pit-fall" bioassay used for many stored-product beetles (see Burkholder and Ma, 1985). The beetles are excellent fliers and, presumably, find and colonize new host sites in the field through flight activity.

One necessary condition for a successful bioassay was that the beetles in the wind tunnel be starved for a number of hours before tests were conducted. When beetles were transferred from their food medium into the wind tunnel, they would quickly form aggregations in the corners and then become motionless. After several hours, a few beetles would begin to move about and take flight spontaneously. This dispersal from the aggregations became more pronounced with time, and responses to pheromone or food baits occurred only after this flight activity had begun. By starving the beetles for 16 hours prior to beginning tests, responses occurred rapidly enough ($>10$ per 3-min period) to be useful for monitoring pheromone isolation.

The aggregation pheromone could be obtained from the beetles either by extracting whole cultures of the insects (Example 2) or by collecting volatiles from a culture (Example 3). Initial experiments and synergism studies were conducted with the whole extracts.

The pheromone is produced by male beetles. When an extract of a culture containing only males was tested against an equivalent extract derived from females, the beetles in the wind tunnel flew preferentially to that from males. The total bioassay counts were 71 and 1, respectively, over eight 10-min observation periods (ca. 1 beetle-equivalent per test). However, both male and female beetles responded readily to the pheromone. In one experiment, the beetles attracted to a culture of males were captured and sexed; of the 142 beetles which responded, 62 were males and 80 were females. The remaining data submitted here represent totals over both sexes.

A methylene chloride extract of culture cups with males was fractionated on silicic acid; but qualitatively, each of the five fractions was inactive in the bioassay compared with the original extract. However, the recombined fractions were again quite attractive, indicating the active compounds had eluted from the column but that more than one chemical was required for attraction. Collection of volatiles from living beetles (Tenax collection) gave similar results.

It was suspected that both male-derived and diet-derived volatiles were responsible for the activity of the culture cups. To identify which fraction of the male-derived extract contained the pheromone, we tested combinations of the five chromatographic fractions (described in Example 4). In each combination, one of the fractions was derived from cultures with only males and the remaining four from cultures with only females. Each combination was tested against the whole extract of the female culture (the control in this experiment). Thus, all the bioassay treatments would contain the full complement of diet compounds as well as any "general" metabolites produced by beetles of both sexes and compounds from any associated microorganisms. The combination of fractions would be expected to differ from the control only if the single male-derived fraction contained the pheromone. From Table I, it is clear that the hexane fraction was the primary source of male-specific attractants. The pheromone was quite nonpolar, indicative of hydrocarbons. Furthermore, only one male-derived fraction was required for potent pheromonal activity. Thus the pheromone appeared not to include components of widely different polarity.

The male-derived attractant was synergized by a wide variety of host volatiles besides those from the rearing medium (Table II). Effective coattractants included crude plant materials, various yeast cultures, single chemicals (especially esters), and mixtures of chemicals. It is noteworthy that the best previously reported attractant (ethanol, ethyl acetate, and acetaldehyde) attracted over three times more beetles when the pheromone was added to it. Because reproduction occurs at feeding sites in these beetles, the enhanced attraction to combined host- and beetle-derived volatiles is undoubtedly of great ecological importance.

The active compound from the male beetles appeared to have at least one double bond, because the 10% ether-hexane fraction from the $AgNO_3$ column contained most of the activity (Table III). A hydrocarbon without double bonds would have eluted with hexane. Further purification by HPLC with the size-exclusion column yielded two consecutive 1-ml fractions that were quite active (Table III). The size-exclusion column was very valuable for separating inert hydrocarbons of high molecular weight from the attractants. Male-derived Tenax collections also provided active hydrocarbons, and these were fractionated by HPLC on the $AgNO_3$ column. Four consecutive 0.5-ml fractions had activity (Table III). As with the open column, the retention of active fractions indicated unsaturation in the pheromone.

Parallel chromatographic fractions derived from female beetles were prepared, and the fractions from both sexes were analyzed by GC. In the active, male-derived HPLC fractions there were at least 10 compounds that were absent from the females (Table IV).

TABLE I

Activity of Silica Fractions of Male-Derived Extract in Wind Tunnel

| Male-Derived Fraction | Mean Bioassay Count (n = 6) | |
|---|---|---|
| | Fraction Combination[a] | Control[b] |
| Hexane | 23.3* | 0.5 |
| 5% Ether-hexane | 1.5 | 0.5 |
| 10% Ether-hexane | 1.5 | 1.8 |
| 50% Ether-hexane | 1.2 | 0.8 |
| 10% MeOH—$CH_2Cl_2$ | 2.2 | 1.3 |

[a]Each male-derived fraction was combined with the four complementary fractions derived from females. The only significantly active combination is marked with an (*).
[b]The control for this experiment was the whole extract of a culture of females. Therefore, each bait in the experiment contained all the same diet-derived compounds, as well as any compounds shared by both sexes of beetles.

TABLE II

Synergist Interactions Between Host Plant Volatiles and Pheromones of *Carpophilus hemipterus*

| Volatile | Mean bioassay count (n >= 8) | | |
|---|---|---|---|
| | Volatile | Pheromone | Volatile + Pheromone |
| Crude Host Materials | | | |
| Orange juice * | 0.5 | 1.0 | 10.6 |
| Apple juice * | 1.2 | 1.3 | 15.6 |
| Juice of corn kernels * | 0.1 | 2.4 | 6.3 |
| Corn silk | 0.0 | 4.5 | 8.8 |
| Corn husk | 0.0 | 2.8 | 8.2 |
| Corn kernel | 0.0 | 2.5 | 13.2 |
| Corn kernel + silk | 0.5 | 3.0 | 21.0 |
| Baker's yeast on agar medium * | 0.4 | 1.9 | 6.3 |
| Baker's yeast on banana | 2.2 | 3.5 | 26.8 |
| Z.b. on banana | 3.2 | 3.0 | 22.8 |
| Esters | | | |
| Methyl acetate * | 1.5 | 6.1 | 21.3 |
| Methyl propionate | 5.3 | 2.0 | 42.5 |
| Methyl butanoate | 6.2 | 1.5 | 44.8 |
| Methyl pentanoate | 0.8 | 4.0 | 29.5 |
| Ethyl acetate * | 0.3 | 2.9 | 14.7 |
| Ethyl propionate * | 1.4 | 5.2 | 35.9 |
| Ethyl butyrate * | 0.3 | 2.4 | 18.7 |
| Propyl acetate * | 1.0 | 2.6 | 17.2 |
| iso-propyl acetate * | 1.4 | 7.0 | 25.4 |
| Propyl propionate | 2.5 | 2.5 | 72.0 |
| Butyl acetate * | 0.1 | 2.7 | 10.6 |
| iso-Butyl acetate | 0.0 | 2.2 | 12.8 |
| sec-Butyl acetate | 0.2 | 2.8 | 3.5 |
| tert-Butyl acetate | 0.0 | 2.8 | 1.5 |
| Butyl propionate | 0.0 | 10.0 | 34.0 |

TABLE II-continued
Synergist Interactions Between Host Plant Volatiles and Pheromones of *Carpophilus hemipterus*

| | Mean bioassay count (n >= 8) | | |
|---|---|---|---|
| Volatile | Volatile | Pheromone | Volatile + Pheromone |
| Pentyl acetate * | 1.7 | 3.0 | 14.3 |
| Heptyl caproate * | 0.4 | 1.0 | 8.3 |
| Octyl acetate * | 0.4 | 2.6 | 13.6 |
| Other Single Components | | | |
| Ethanol * | 0.4 | 4.5 | 32.1 |
| 1-Butanol * | 0.1 | 2.6 | 8.0 |
| 1-Heptanol * | 0.2 | 1.6 | 5.5 |
| Acetaldehyde * | 0.0 | 2.4 | 7.8 |
| Propanal * | 0.8 | 2.4 | 7.0 |
| 2-Pentanone * | 0.2 | 0.8 | 7.7 |
| Acetic acid * | 0.3 | 3.0 | 8.7 |
| Lactic acid * | 0.6 | 2.5 | 8.7 |
| Mixtures (all 1:1:1) | | | |
| Ethanol:acetaldehyde: ethyl acetate * | 9.2 | 4.5 | 29.6 |
| Ethanol:ethyl butyrate: lactic acid * | 2.1 | 2.2 | 32.4 |
| Ethanol:ethyl propionate: propionic acid * | 8.9 | 5.0 | 43.9 |
| Ethanol:ethyl propionate: acetaldehyde * | 6.6 | 3.9 | 28.2 |
| Ethanol:ethyl iso-butyrate: lactic acid * | 2.1 | 2.2 | 32.4 |

Each line represents one experiment; data are mean counts per 3-min test. When the volatile name is followed by an (*), the experiment was a balanced incomplete block involving only the three treatments indicated in column headings; otherwise, the means were taken from experiments involving other experimental designs and often having additional treatments not listed here. Baker's yeast = *Saccharomyces cerevisiae*; the agar medium was potato dextrose agar. Z.b. = *Zygosaccharomyces bailii*. The "pheromone" was the hydrocarbon fraction from an extract of a culture of male beetles; the concentration was adjusted so that there was 0.5-1.0 ng of the major pheromone component per test; but in each line of the table the amount of pheromone used was constant.

TABLE III
Activity of Chromatographic Fractions Derived from Male *C. hemipterus* Hydrocarbons[a]

| | Mean Bioassay Count (n = 4) | |
|---|---|---|
| Fraction Description | Fraction + Coattractant[b] | Coattractant[b] |
| AgNO₃ fractions (open column, from culture extract) | | |
| Hexane | 1.0 | 1.3 |
| 5% Ether-hexane | 15.0* | 2.0 |
| 10% Ether-hexane | 33.3* | 1.3 |
| 25% Ether-hexane | 6.7 | 2.5 |
| Ether (first) | 1.3 | 2.0 |
| Ether (second) | 0.8 | 1.0 |
| Size-exclusion fractions (HPLC, from AgNO₃ 10% ether-hexane fraction, above) | | |
| 8-10 ml after injection | 0.8 | 1.0 |
| 10-11 ml | 12.0* | 1.5 |
| 11-12 ml | 9.3* | 1.0 |
| 12-13 ml | 3.0 | 1.0 |
| 13-14 ml | 1.0 | 1.8 |
| 14-15 ml | 1.0 | 1.3 |
| 15-16 ml | 1.5 | 1.0 |
| AgNO₃ fractions (HPLC, from Tenax collections) | | |
| 3.0-4.5 ml after injection | 0.0 | 0.3 |
| 4.5-5.0 ml | 0.0 | 0.0 |
| 5.0-5.5 ml | 0.5 | 0.0 |
| 5.5-6.0 ml | 12.8* | 0.3 |
| 6.0-6.5 ml | 12.0* | 0.0 |
| 6.5-7.0 ml | 25.8* | 0.8 |
| 7.0-7.5 ml | 4.8* | 0.3 |
| 7.5-8.0 ml | 0.8 | 0.3 |

[a]Hydrocarbons were isolated by column chromatography on silica prior to separations listed in Table.
[b]In first two data sets, coattractant was the extract from female beetles − diet; in the last experiment, coattractant was propyl acetate (10% in mineral oil, 10 μl per test.

Considering both the GC and bioassay data, it was clear that no single compound was absolutely required for activity and that more than one subset of male-specific hydrocarbons was sufficient to elicit attraction. However, complete separation of these compounds was not obtained by any HPLC method. Preparative GC did not provide pure compounds either, because many were too similar in GC retention and too labile to survive this technique.

In the extracts of male cultures, 1 beetle equivalent contained approximately 1 ng of the major component (I=13.83, Table IV). In a typical Tenax collection, 1 beetle-day represented ca. 0.5 ng of this component. Because the beetles could live for several months in the aeration flasks, the Tenax collections were the richer source of active hydrocarbons and, furthermore, these were relatively easy to purify.

Mass spectra of the unknown compounds were obtained (Example 5). The EI mass spectrum of the most abundant compound suggested the molecular weight to be 176. This was confirmed by the CI mass spectrum, in which the major peaks were 177 (M+1) and 233 (M+57, due to the isobutane reagent gas). The molecular weight is consistent with the molecular formula $C_{13}H_{20}$, indicating four double-bond equivalents. There was no evidence for oxygen or other heteroatoms in the mass spectrum. All fragment ions had reasonable $C_xH_y$ formulae, and the chromatographic evidence favored a hydrocarbon also. The other male-specific peaks had similar mass spectra, indicating hydrocarbons of 13, 14, or 15 carbons, all with four double-bond equivalents (Table IV). Based on hydrogenation studies, mass spectra, ultraviolet spectra, and NMR spectra, it was evident that the aggregation pheromone complex of *C. hemipterus* was comprised of unsaturated hydrocarbons of the general structure:

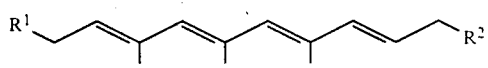

TABLE IV

| Male-Specific Hydrocarbons in *C. hemipterus* | | | | |
|---|---|---|---|---|
| Retention Index (I)[a] | Relative Amount | Molecular Weight | HPLC Retention (ml)[b] | |
| | | | Size Exclusion | AgNO$_3$ |
| 12.44 | 3% | 176 | (not detected) | 6.0–6.5 *[c] |
| 13.08d | 11% | 176 | 10.5–11.5 * | 6.0–6.5 * |
| 13.29[d] | 4% | 176 | 11.0–12.0 * | 5.0–5.5 |
| 13.83 | 57% | 176 | 11.0–12.0 * | 6.5–7.5 * |
| 14.22 | 4% | 190 | 10.0–11.0 * | 5.5–6.5 * |
| 14.28 | 3% | 190 | 10.5–11.5 * | 5.5–6.5 * |
| 14.63 | 7% | 190 | 10.5–11.5 * | 6.5–7.0 * |
| 14.76 | 8% | 190 | 11.0–12.0 * | 6.0–7.0 * |
| 14.91 | 1% | 204 | 10.0–11.0 * | 6.0–6.5 * |
| 15.15 | 2% | 204 | 10.0–11.0 * | 5.5–6.0 * |

[a]Retention index relative to n-alkanes: determined from temperature programmed runs (10°/min) by linear interpolation.
[b]Based on examination of fractions by GC. Many retention volumes represent two consecutive HPLC fractions which both contained the compound.
[c](*) indicates that HPLC fraction was active in bioassay.
[d]Also appears in every fraction where the major hydrocarbon (I = 13.83) occurs; these may be decomposition products.

wherein $R^1$ and $R^2$ are independently selected from hydrogen or lower alkyl (Examples 5–8).

These structures were confirmed by synthesis from known compounds by the general procedure illustrated below, in which compound 9a represents the active pheromone compounds. The synthetic compounds were identical in all respects with the natural pheromone components.

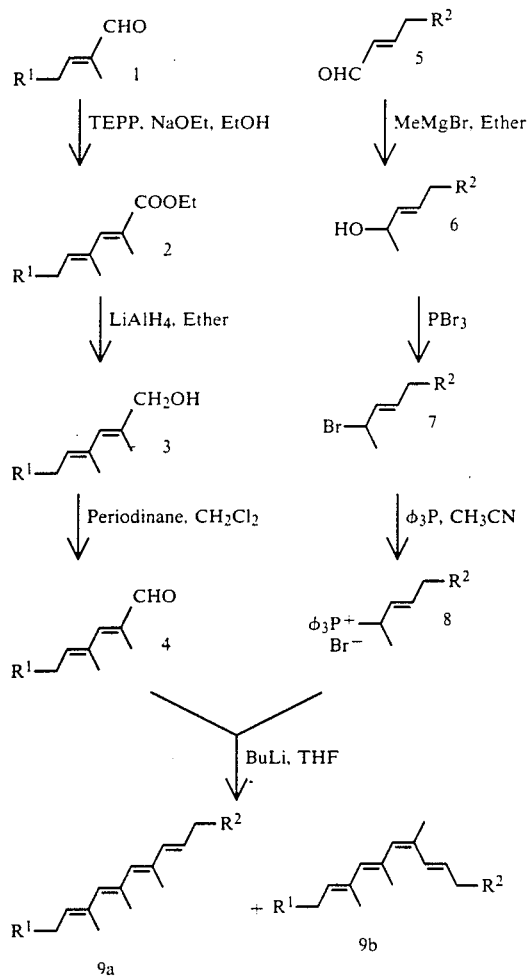

The reactions were performed as described in the literature for similar systems. Except for the Wittig salt, each intermediate product was used in the next reaction without purification, other than drying over sodium sulfate and removing the solvent. By GC, reaction yields usually exceeded 90%; minor side products were carried into subsequent reactions rather than trying to separate them from the relatively labile products by distillation.

In the synthesis of the C-13 pheromone ($R^1$=H and $R^2$=H), tiglic aldehyde 1 (2-methyl-(E)-2-butenal) was converted to the ethyl ester of the 8-carbon acid 2 in a Wittig-Horner condensation with triethyl 2-phosphonopropionate, using the procedure of Gallagher and Webb (1974). This reaction is primarily (E)-directed (Boutagy and Thomas, 1974), and by GC only one isomer was observed. The ester was reduced with LiAlH$_4$ to the alcohol 3 as described by Mori (1976) for a different ethyl ester. The alcohol was then oxidized to the aldehyde 4 with the periodinane reagent of Dess and Martin (1983). The other half of the target hydrocarbon was constructed by alkylating crotonaldehyde 5 ((E)-2-butenal) with methylmagnesium bromide to form the alcohol 6, as described by Brooks and Snyder (1955), except that a commercially prepared Grignard reagent was used. The alcohol was converted to the bromide 7 with PBr$_3$ by the procedure of Noller and Dinsmore (1943), except that the bromide was recovered by extraction with hexane rather than by distillation. The secondary, allylic bromide was treated with triphenylphosphine in refluxing acetonitrile to produce the phosphonium salt 8. This salt was crystallized by washing the product repeatedly with dry ether. Finally, the aldehyde 4 and the phosphonium salt 8 were linked in a Wittig reaction (Sonnet, 1974) to form the isomers of the conjugated tetraene 9a and 9b. Initial purification was on silica, elution with hexane. There appeared to be some decomposition on this column (formation of yellow color, which remained on the column), but both isomers were recovered.

These isomers were completely resolved by HPLC on the AgNO$_3$ column. The (E,E,Z,E) isomer eluted at 5.5 ml after injection, and the (E,E,E,E) isomer at 6.5 ml.

The C-14 pheromone component ($R^1$=H, $R^2$=CH$_3$) was synthesized by the same scheme, except that (E)-2-pentenal ($R^2$=CH$_3$) was substituted for crotonaldehyde ($R^2$=H) as structure 5.

Both synthetic tetraenes were active in the bioassay (Table V). The major compound in the beetles, 3,5,7-trimethyl-(E,E,E,E)-2,4,6,8-decatetraene, showed significant synergistic activity with propyl acetate, although it was not active by itself at the level corresponding to one male equivalent. The 14-carbon minor component, 3,5,7-trimethyl-(E,E,E,E)-2,4,6,8-undecatetraene, was also synergistic with propyl acetate and, in addition, was significantly active by itself. Surprisingly, the 14-carbon compound was more active than the 13-carbon compound, even when tested at one-fifth the dose. The 14-carbon compound is a minor constituent in the male-derived hydrocarbons (normally about one-fifth as abundant as the major component), but it accounts for a large proportion of the pheromonal activity. Furthermore, these hydrocarbons synergize each other in much the same way as host-derived volatiles synergize the whole pheromone.

The fourth experiment in Table V demonstrates in another way that just the major, 13-carbon component is insufficient for maximum activity. This compound attracted only about one-third as many beetles as the whole, male-derived hydrocarbon mixture. However, when the 14-carbon component was added to the 13-carbon tetraene, the combination compared favorably with the male-derived attractant (fifth experiment, Table V).

The final experiment in Table V shows the most active composition tested, C-14 synthetic in combination with ethanol, ethyl acetate, and acetaldehyde, the food volatile attractant reported by Smilanick et al. (1978).

TABLE V

Bioassay Activity of Synthetic Hydrocarbons

| Treatment[a] | Mean Bioassay Count[b] |
|---|---|
| Activity of $C_{13}$ synthetic (n = 12) | |
| Control | 0.1 c |
| $C_{13}$ synthetic (1 ng) | 0.5 bc |
| Propyl acetate (coattractant) | 0.8 b |
| $C_{13}$ synthetic (1 ng) + propyl acetate | 5.7 a |
| Activity of $C_{14}$ synthetic (n = 12) | |
| Control | 0.1 c |
| $C_{14}$ synthetic (1 ng) | 1.8 b |
| Propyl acetate | 2.0 b |
| $C_{14}$ synthetic (1 ng) + propyl acetate | 23.2 a |
| Comparative activities of $C_{13}$ and $C_{14}$ synthetics (n = 12) | |
| Propyl acetate | 1.3 d |
| $C_{13}$ synthetic (1 ng) + propyl acetate | 4.7 c |
| $C_{14}$ synthetic (200 pg) + propyl acetate | 14.1 b |
| $C_{13}$ + $C_{14}$ synthetics (1 ng + 200 pg) + propyl acetate | 25.0 a |
| Comparison of male-derived hydrocarbons with $C_{13}$ synthetic (n = 8) | |
| Propyl acetate | 0.4 c |
| Propyl acetate + $C_{13}$ synthetic (1 ng) | 5.5 b |
| Propyl acetate + male-derived hydrocarbons (1 ng of major, 13-carbon component) | 18.0 a |
| Comparison of male-derived hydrocarbons with combined $C_{13}$ and $C_{14}$ synthetics (n = 8) | |
| Propyl acetate | 3.3 b |
| Propyl acetate + $C_{13}$ + $C_{14}$ synthetics (1 ng + 200 pg) | 27.5 a |
| Propyl acetate + male-derived hydrocarbons (1 ng of major, 13-carbon component) | 24.4 a |
| Comparative activity of $C_{14}$ synthetic combined with ethanol, ethyl acetate, and acetaldehyde (n = 12) | |
| Ethanol, ethyl acetate, acetaldehyde (10 μl, | 7.95 b |
| $C_{14}$ synthetic (1 ng) | 0.80 c |
| $C_{14}$ synthetic (1 ng) + ethanol, ethyl acetate, acetaldehyde (10 μl, 10% in mineral oil) | 31.22 a |

[a] $C_{13}$ synthetic = 3,5,7-trimethyl-(E,E,E)-2,4,6-decatetraene; $C_{14}$ synthetic = 3,5,7-trimethyl-(E,E,E)-2,4,6,8-undecatetraene; propyl acetate was the coattractant in all experiments (used as 10% solution in mineral oil, 10 μl per test); male-derived hydrocarbons were from Tenax collection, hexane fraction from silica, amount tested contained 1 ng of the major, 13-carbon component.
[b] Each experiment was a balanced incomplete block, with the treatments tested in pairs. Tests lasted 3 min. Analysis was in the log (X + 1) scale, conducted by the method of Yates (1940). Means converted back to the numerical scale for presentation. In each of the five experiments, means followed by the same letter are not significantly different (LSD, 0.05).

The importance of olfaction in the behavior of insects is well known. Insect-produced volatiles, e.g., pheromones, and host plant odors may facilitate location of conspecifics for mating and orientation to acceptable host plants for feeding and oviposition. Pheromones, which may be attractive alone, may have their activity enhanced or synergized by host plant odors which show little attraction when presented alone.

With the identification of the driedfruit beetle pheromones and synergists therefor, a tool is available to monitor beetle populations for directing insecticide applications and evaluating control measures. The synergized pheromones may also be potentially used in trap-out strategies.

A synergist is herein defined as a material that enhances the activity of other materials, so that the overall activity of the mixture is greater than the sum of the individual components.

An effective synergist for an attractant pheromone is useful in several ways:

1. A synergist improves population monitoring with the pheromone by increasing the attractiveness of the pheromone.

2. A synergist improves attractiveness of the pheromone, thus facilitating trap-out strategies.

3. An inexpensive synergist reduces the cost of insect control, since its addition to the pheromone in traps decreases the quantity of costly pheromone needed and extends the longevity of the attractive bait.

The potency of these synergized pheromone compositions dictates that they be applied in conjunction with a suitable inert carrier or vehicle as known in the art. Of particular interest are those which are agronomically acceptable. Alcohols, hydrocarbons, halogenated hydrocarbons, glycols, ketones, esters, aqueous mixtures, and solid carriers such as clays, cellulose, rubber, or synthetic polymers are illustrative of suitable carriers. The synergized pheromone compositions may be used in a number of ways, e.g., in combination with pesticides to kill the insects or in traps to monitor population changes or to kill insects in the traps. Other formulations and methods of use will be obvious to skilled artisans.

The synergized pheromone compositions encompassed herein are effective in attracting a variety of organisms. Without desiring to be limited thereto, pests of particular interest known to be susceptible to treatment are agronomically important insects, especially the nitidulid species C. hemipterus and C. lugubris.

A preferred synergized pheromone composition contemplated by this invention for use in insect traps comprises a mixture of 3,5,7-trimethyl-(E,E,E)-2,4,6,8-undecatetraene and ethanol, ethyl acetate, and acetaldehyde.

A second preferred synergized pheromone composition contemplated by this invention for use in insect traps comprises a mixture of 3,5,7-trimethyl-(E,E,E)-2,4,6,8-decatetraene, 3,5,7-trimethyl-(E,E,E)-2,4,6,8-undecatetraene, and propyl acetate or propyl propionate. It will be obvious to skilled workers in the insect pheromone field that the ratio and absolute amounts of active ingredients may be varied depending upon environmental conditions such as temperature, humidity, wind velocity, and insect population.

The following examples as intended only to further illustrate the invention and are not intended to limit the scope of the invention which is defined by the claims.

EXAMPLE 1

Bioassay Method

All bioassays were conducted in a wind-tunnel olfactometer constructed of Plexiglas 0.60 × 0.60 m in cross section and 1.35 m long. The floor was plywood, which was rough enough in texture to allow any beetles that had fallen on their backs to right themselves. The ends were covered with 30-mesh steel screen. An electric fan was connected by a duct to the upwind end; air was drawn from the room and forced through the wind tunnel. Laminar flow was achieved by passing the air through several layers of cheesecloth mounted outside the upwind screen, as described by Baker and Linn (1984). The linear air flow rate was 0.3 m/sec. The temperature was kept at 27°; the relative humidity was not controlled but was in the range of 30-40%. The wind tunnel was lighted from above with four 40-watt fluorescent tubes.

About 24 hr before bioassays were to begin, cultures containing a total of 200-400 beetles, about 1 week old, were placed in a fume hood for 8 hr, during which the diet medium dried down to about 75% of its original volume. The beetles were then transferred to the wind tunnel and kept without food for an additional 16 hr. Lights and air flow were left off during this time but were turned on before beginning bioassays. Beetles were never observed to fly to a bait unless they had been starved for a number of hours. For good responsiveness, the beetles had to have been without food but not unduly stressed. With the above procedure, the beetles appeared healthy and usually began to respond to attractive baits within 1 hr of turning on the wind-tunnel lights and fan. Once the beetles were ready, as many as 30-50 three-minute tests could be run in the course of a day.

Test baits were suspended from a horizontal wire 0.4 m above the floor of the wind tunnel, perpendicular to the air flow and 0.2 m from the upwind screen. Baits were always tested in pairs, separated by 0.3 m. Extracts or chromatographic fractions to be used as baits were applied to 7-cm circles of filter paper which were folded into quarters and secured with a paper clip. Concentrations of test solutions were adjusted so that the application volume was in the range of 10-30 $\mu$l. Because of the location of the baits, beetles could reach them only by flying. The test period was 3 min; during this time the number of beetles landing on each bait was recorded. Tests were always replicated and each bait was tested in both positions, so that any position effects would not bias comparisons of treatments. Tests were separated in time by 2-5 min.

EXAMPLE 2

Extraction

Beetles to be extracted were immobilized over ice and separated by sex within 7 days of emergence; then they were returned to rearing cups until extraction. The 30-ml plastic rearing cups normally contained up to 100 beetles and ca. 10 ml of the pinto bean rearing medium.

As a typical example of an extraction, 300 male beetles, 9-12 days old, and the diet medium from the 4 rearing cups which held these were soaked in 100 ml of methylene chloride for 15 min. The extraction was repeated twice more, and the combined extracts were filtered and dried over sodium sulfate. The extract was reduced in volume to 10 ml by rotary evaporation. Concentrations were calculated as beetle equivalents per ml, based on counts of beetles and extract volumes.

EXAMPLE 3

Volatile Collection

A 50-ml filtering flask was fitted with a cork into which a Tenax trap was inserted. The Tenax trap was prepared from a 10 cm×0.5 cm (ID) piece of soft glass tubing. A piece of brass screen (100 mesh) was sealed into the end by heating. The tube was filled to a depth of 0.5 cm with Tenax porous polymer (60/80 mesh, Alltech, Deerfield, Ill.) which had been cleaned by extraction with hexane in a Soxhlet apparatus. The Tenax was held in place by a plug of glass wool. About 15 ml of pinto bean diet were placed into the flask, and the tip of the Tenax trap was adjusted to about 1 cm above the diet. A vacuum was applied to the Tenax trap so that volatiles within the flask were drawn into the trap. A second Tenax trap was attached to the side arm of the flask to clean the air drawn into the flask. This connection was made with "Teflon" tubing. Approximately 100 male beetles were added to the flask, and the air flow through the flask was adjusted to 50 ml/min. The flask was kept in an incubator at 27° and 40% relative humidity. At this humidity the diet dried out slowly over a week; with the diet in this condition, the beetles remained active and healthy, but the growth of mold was retarded. The beetles received 14 hr of light each day. Eighteen such flasks were operated in the incubator at one time. Pheromone collections were quantified in terms of beetle-days, defined as the average amount of pheromone collected from one beetle in one day. Volatile collections were also made from female beetles and from diet medium without beetles.

To extract volatiles from the Tenax traps, each trap was rinsed three times with 200 $\mu$l hexane. Before returning the trap to its flask, air was passed through the trap to evaporate residual solvent. Traps were rinsed every 2 or 3 days. The extracts were set aside for chromatography.

EXAMPLE 4

Chromatography

Column chromatography on silicic acid was used for all initial purifications. Columns were usually 5 cm by 0.5 cm, and these were adequate for extracts with 100 beetle equivalents, including diet medium. Before chromatography the methylene chloride was carefully removed from these extracts under nitrogen, and the samples were taken up in hexane. Columns were eluted with 2 column volumes each (2 ml) with these solvents: hexane; 5%, 10%, and 50% ether in hexane; and 10% methanol in methylene chloride. Each solvent was collected as a separate fraction. Larger columns were used for extracts with greater numbers of equivalents.

The rinses from the Tenax traps were also applied to these silicic acid columns; a collection 3000 beetle-days in size did not overload a 5 cm×0.5 cm column.

Silicic acid containing 25% $AgNO_3$ was also used as a packing in open columns (5 cm×0.5 cm). The samples were applied in hexane and the columns eluted with hexane; 5%, 10%, and 25% ether in hexane; and finally, with ether.

All chromatographic separations and syntheses were monitored by gas chromatography (GC) using a Varian 3700 gas chromatograph. It was equipped with flame ionization detector, splitless injector for capillary columns, effluent splitter for preparative GC on a packed column, and effluent collector (Brownlee and Silverstein, 1968). Two columns were used: The first was a 15 m×0.25 mm (ID) DB-1 capillary with a 1.0 $\mu$m film thickness (J & W Scientific, Folsom, Calif.). For many samples, this column was programmed from 100° to 200° at 10° per min, although cooler starting temperatures or hotter final temperatures were sometimes required. Beetle-derived samples were usually concentrated by 20-100 times by evaporation under $N_2$, so that the 1-2 $\mu$l injections would have enough material to be easily detected (>1 ng per component). The other column, used for preparative GC, was a 2 m×2 mm (ID) glass column, packed with 3% OV-101 on Chromosorb WHP 100/200 (Alltech). The gas chromatograph was interfaced to a Hewlett-Packard 3396A integrator.

Retention indices (I) relative to n-alkane standards were determined for the male-specific hydrocarbons. The DB-1 column was programmed from 100° to 200° at 10° per min, and the retention indices calculated by linear interpolation (Poole and Schuette, 1984, pp. 23–25).

High performance liquid chromatography (HPLC) was conducted isocratically using a Waters Associates model 6000 pump and R401 refractometer detector. Two columns were used. The first was a 30 cm×0.75 cm (ID) PLGEL 50A 10 $\mu$m size-exclusion column (Polymer Laboratories, Shropshire, UK), and it was eluted with hexane. The other column was a 25 cm×0.46 cm (ID) Lichrosorb Si60 silica column (5 $\mu$m particle size) (Alltech), coated with $AgNO_3$ as described by Heath and Sonnet (1980). This column was eluted with 25% toluene in hexane. The void volumes for the two columns were estimated to be 8 and 3.5 ml, respectively. The beetle-derived samples were not concentrated enough to be detected by the refractometer. Effluent was collected as 1-ml or 0.5-ml fractions, which were later analyzed by GC and bioassayed.

EXAMPLE 5

Spectra

Mass spectra were obtained on a Finnigan 4535 quadrupole mass spectrometer. Sample introduction was always by GC (DB-1 capillary). An ionizing potential of 70 eV was used for electron impact spectra. NMR proton spectra were obtained on a Bruker 300 mHz instrument. Samples were dissolved in deuterobenzene and shifts were calculated relative to tetramethylsilane. Further experimental details are given with results. Ultraviolet spectra were taken with a Perkin Elmer (Norwalk, Conn.) Lambda 4B high performance UV spectrophotometer. The solvent was hexane.

EXAMPLE 6

Hydrogenation of C-13 Compound

Saturated derivatives of male-derived hydrocarbons were prepared by the method of Parliment (1973), except that methylene chloride was used as the solvent. Palladium (10%) on carbon was used as the catalyst in the initial reactions, but $PtO_2$ was later found to be preferable because it caused less formation of cyclic side products. The saturated derivatives were analyzed by mass spectrometry to gain structural information about the carbon skeletons.

By GC, hydrogenation of the major, 13-carbon compound over Pd produced at least 12 distinct compounds. The key products had molecular weights of 184; the uptake of 8 hydrogens indicated the existence of 4 double bonds and no rings (if no triple bonds). However, other products had molecular weights of 182 and would not hydrogenate further. Apparently, cyclic rearrangement competed with simple hydrogenation. $PtO_2$ as catalyst gave a greater proportion of the acyclic product, which was more useful for structure elucidation.

Mass chromatograms were prepared for the ions in the series, $C_nH_{2n+1}^+$, n=4, ..., 12. These fragments, m/z=57, 71, 85, ..., 169, were the dominant features for the acyclic products but were nearly absent from the cyclic products (which had $C_nH_{2n-1}^+$ as the primary series). Based on the mass chromatograms, there were four acyclic products (two of which were poorly resolved on the DB-1 capillary), and these all had nearly identical mass spectra.

The intensities of the $C_nH_{2n+1}$ peaks, especially those of higher mass, give structural information about branched alkanes (Nelson, 1978). These tend to fragment at branch points, with the secondary carbonium ion retaining the charge. Compared with the spectrum for tridecane, the peaks at 155, 141, 113, and 99 were relatively enhanced, while those at 127 and 85 were relatively suppressed. These data suggested that the saturated derivative was 3,5,7-trimethyldecane.

3,5,7-Trimethyldecane possesses three asymmetric centers. If the original compound had double bonds involving the 3, 5, and 7 positions, then catalytic hydrogenation would create these asymmetric centers without stereoselectivity. The resulting eight optical isomers would produce at most 4 GC peaks on an achiral column, which is what we observed.

EXAMPLE 7

UV Spectrum of C-13 Compound

The UV spectrum possessed a maximum at 274 nm ($\epsilon = 4.9 \times 10^4$), which was similar to that observed for the terpene, alloocimene (2,6-dimethyl-2,4,6-octatriene), with a maximum absorbance at 276 nm. The UV spectrum indicated that the unknown was highly conjugated, but because steric and other factors can affect UV absorbance (Silverstein and Bassler, 1967), the exact number of double bonds in conjugation was not clear.

EXAMPLE 8

NMR Spectrum of C-13 Compound

The NMR spectrum provided important structural information, but handling the samples proved to be difficult. The initial NMR sample of about 20 $\mu$g was prepared by preparative GC. The purity of this sample was only 72% by capillary GC, primarily because the target compound rearranged or decomposed to a significant extent on the preparative GC column. Nevertheless, the largest impurity was only 7% of the sample, so useful NMR data could be obtained. This sample was contained in a capillary NMR tube and was scanned 30,000 times. A subsequent NMR sample, containing about 30 $\mu$g, was prepared by HPLC on the size-exclusion column. After evaporating the hexane and adding deuterobenzene, the sample was 90% pure by capillary GC. This sample was held in a standard (5 mm) tube, and 3200 scans provided a good-quality spectrum.

The spectra were difficult to interpret because the unknown compound rearranged, polymerized, or both during acquisition of the spectra (in the latter sample, totally). Peaks belonging to the original compound were differentiated from those due to decomposition by observing changes in the spectra over time. At first, no peaks were present in the region 0.8–1.4 ppm; but over time, peaks in this area grew to become the dominant spectral features. Nevertheless, both NMR samples produced identical spectra when the artifact peaks were ignored. The observed resonances were: 6.25 (1H, dq, J=15.4, 2), 6.03 (2H, br s), 5.63 (1H, dq, J=15.4, 6.7), 5.53 (1H, qq, J=6.7, 1), 2.00 (3H, br s), 1.98 (3H, br s), 1.74 (3H, br s), 1.73 (3H, d [half concealed], J=6.7), and 1.64 (3H, d, J=6.6). All the resonances appeared to represent either olefinic protons or olefinic methyl groups. The data suggested that the compound was 3,5,7-trimethyl-2,4,6,8-decatetraene. The double bond at the 8 position had the (E) configuration because of the large coupling constant (J = 15.4 Hz) between the olefinic protons, but the configurations at the three trisubstituted double bonds were not determined.

EXAMPLE 9

(1-Methyl-(E)-2-butenyl)triphenylphosphonium Bromide (Compound 8, $R^2$=H)

In this and following synthesis examples, the compounds and reagents for chemical synthesis were obtained from Aldrich Chemical Co. (Milwaukee, Wis.) and were used as received. Solvents were dried over 4A molecular sieves, except ether, which was dried over sodium metal.

Compound 8, $R^2$=H was prepared from triphenylphosphine (Aldrich) and 4-bromo-2-pentene, Compound 7, $R^2$=H, which was previously reported by Mulliken et al. (1935).

Triphenylphosphine (3.1 g, 0.012 mole) and 4-bromo-(E)-2-pentene (1.7 g, 0.011 mole) were added to 40 ml dry (molecular sieve) acetonitrile and refluxed for 6 hr. The solvent was removed by rotary evaporation, and the sticky product was washed three times with dry ether. Further traces of ether were removed under rotary evaporation, and the product was placed in a vacuum desiccator for 2 hr, where it became a friable white solid. Alternatively, the salt crystallized after repeated (>20) washings with dry ether, but the method using the vacuum desiccator was quicker and provided an acceptable reagent for the Wittig reaction.

EXAMPLE 10

3,5,7-Trimethyl-(E,E,E)-2,4,6,8-decatetraene (Compound 9a; $R^1$=H, $R^2$=H)

(1-Methyl-(E)-2-butenyl)triphenylphosphonium bromide from Example 9 (0.62 g, 0.0015 mole) was added to a dry flask with 5 ml tetrahydrofuran. The flask was equipped with magnetic stirrer and septum; the reaction was carried out under nitrogen. The salt did not dissolve completely but became a sticky suspension. The mixture was cooled over ice, and butyllithium (2.5M in hexane) was added dropwise, with stirring, until the color change became permanent; then an additional 0.0015 mole was added. The solid in the flask dissolved as it was converted to the ylide. One hundred milligrams of 2,4-dimethyl-(E,E)-2,4-hexadienal (0.0008 mole), compound 4, $R^1$=H, prepared previously by Pattel and Pattenden (1985), was added to the Wittig reagent, and the mixture was allowed to warm to room temperature. The mixture was stirred for 2 hr, and it was again cooled over ice. Water was added dropwise until the red color of the solution had disappeared, and ca. 2 ml more water was added. The mixture was diluted with hexane and the organic layer dried over sodium sulfate. The solvent was removed and the product passed through a silica column with hexane. By capillary GC the product was 61% the (E,E,E,E) isomer, ca. 31% the (E,E,Z,E) isomer, and ca. 8% by-products, after clean-up on silica. Further purification on the AgNO$_3$ HPLC column yielded the (E,E,E,E) isomer in >97% purity.

The (E,E,Z,E) isomer was recognized by its thermal lability. (Conjugated polyenes with internal, (Z), double bonds are very unstable.) By GC on DB-1 (100°-200° at 10°/min), the (E,E,Z,E) isomer produced a rearrangement peak at 3.99, a sharp peak at 5.47, and a broad, poorly defined shoulder between these peaks. The initial peak could be eliminated by setting the injector temperature at 100°, and the shoulder (which indicated on-column thermal rearrangement) could be eliminated by using a thinner film column (0.25 μm vs. 1.0 μm), allowing the compound to elute at a cooler temperature (ca. 115 vs. 155°).

EXAMPLE 11

(1-Methyl-(E)-2-pentenyl) triphenylphosphonium Bromide (Compound 8, $R^2$=CH$_3$)

The compound was prepared from triphenylphosphine and 2-bromo-(E)-3-hexene, a compound which was reported previously (Bianchini and Guillemonat, 1968). Triphenylphosphine (1.6 g, 0.0061 mole) and 2-bromo-(E)-3-hexene (1.0 g, 0.0061 mole) were added to 10 ml dry acetonitrile and refluxed for 6 hr. The solvent was removed by rotary evaporation. The thick, sticky liquid product was stirred with dry ether 4 times, with the ether being decanted. After removing further traces of ether by rotary evaporation, the product was placed in a vacuum desiccator for 6 hr, where the product became a friable white solid (1.6 g, 61%).

EXAMPLE 12

3,5,7-Trimethyl-(E,E,E,E)-2,4,6,8-undecatetraene (Compound 9a, $R^1$=H, $R^2$=CH$_3$)

(1-Methyl-(E)-2-pentenyl)triphenylphosphonium bromide (0.40 g, 0.0009 mole), from Example 11, was added to a flask with 2 ml dry tetrahydrofuran. The reaction was run under nitrogen, and the flask was equipped with a magnetic stirrer. The mixture was cooled over ice, and butyllithium (2.5 m in hexane) was added dropwise until the color change became permanent; then an additional 0.4 ml (0.001 mole) was added. After 5 min, 100 mg (0.0008 mole) of 2,4-dimethyl-(E,E)-2,4-hexadienal (4, $R^1$=H) was added. The mixture was warmed to room temperature, stirred for 2 hr, then cooled over ice again. Water (1 ml) and pentane (3 ml) were added. The aqueous layer was washed twice with 2 ml pentane. The combined organic layers were washed three times with water and dried over Na$_2$SO$_4$. After the product was passed through a silica column with hexane, both the (E,E,E,E) and (E,E,Z,E) isomers were present (47% and ca. 40%, respectively, by GC). The isomers were resolved by HPLC on the silver-nitrate column, as described in Example 10.

It is understood that the foregoing detailed description is given merely by way of illustration and that modification and variations may be made therein without departing from the spirit and scope of the invention.

REFERENCES

Alm, S. R., F. R. Hall, T. L. Ladd, Jr., and R. N. Williams. 1985. A chemical attractant for *Glischrochilus quadrisignatus* (Coleoptera: Nitidulidae). J. Econ. Entomol. 78: 839-843.

Alm, S. R., F. R. Hall, T. P. McGovern, and R. N. Williams. 1986. Attraction of *Glischrochilus quadrisignatus* (Coleoptera: Nitidulidae) to semiochemicals: butyl acetate and propyl propionate. J. Econ. Entomol. 79: 654-658.

Baker, T. C., and C. E. Linn, Jr. 1984. Wind tunnels in pheromone research. In Techniques in Pheromone Research, H. E. Hummell and T. A. Miller, eds., Springer-Verlag, New York, 464 pp.

Bianchini, J.-P., and A. Guillemonat. 1968. Action des acides chlorhydrique et bromhydrique sur les carbures alléniques. Bull. Soc. Chim. Fr. 1968: 2120-2123.

Borden, J. H. 1984. In Insect Communication, T. Lewis, ed., Academic Press, New York, p. 123.

Boutagy, J., and R. Thomas. 1974. Olefin synthesis with organic phosphonate carbanions. Chem. Rev. 74: 87-99.

Brooks, L. A., and H. R. Snyder. 1955. 3-Penten-2-ol. Org. Synth., Coll. Vol. 3: 696-698.

Brownlee, R. G., and R. M. Silverstein. 1968. A micropreparative gas chromatograph and a modified carbon skeleton determinator. Anal. Chem. 40: 2077-2079.

Burkholder, W. E., and M. Ma. 1985. Pheromones for monitoring and control of stored-product insects. Ann. Rev. Entomol. 30: 257-272.

Dess, D. B., and J. C. Martin. 1983. Readily accessible 12-I-5 oxidant for the conversion of primary and secondary alcohols to aldehydes and ketones. J. Org. Chem. 48: 4155-4156.

Dowd, P. F. 1987. A labor saving method for rearing the driedfruit beetle (Coleoptera: Nitidulidae) on pinto bean-based diet. J. Econ. Entomol. 80: 1351-1353.

Gallagher, G., Jr., and R. L. Webb. 1974. Tetrasubstituted acrylates: the Wittig-Horner reaction of ketones with triethyl 2-phosphonopropionate. Synthesis 1974, No. 2: 122-124.

Heath, R. R., and P. E. Sonnet. 1980. Technique for in situ coating of Ag+ onto silica gel in HPLC columns for the separation of geometrical isomers. J. Liq. Chromatog. 3: 1129-1135.

Hinton, H. E. 1945. A Monograph of the Beetles Associated with Stored Products. Jarrold and Sons, Norwich, U.K., 443 pp.

Mori, K. 1976. Synthesis of optically active forms of ipsenol, the pheromone of Ips bark beetles. Tetrahedron 32: 1101-1106.

Mulliken, S. P., R. L. Wakeman, and H. T. Gerry. 1935. The preparation of certain alkenes, alkadienes and alkynes. J. Am. Chem. Soc. 57: 1605-1607.

Nelson, D. R. 1978. Long-chain methyl-branched hydrocarbons: occurrence, biosynthesis and function. Adv. Insect Physiol. 13: 1-33.

Noller, C. R., and R. Dinsmore. 1943. Isobutyl bromide. Org. Synth., Coll. Vol. 2: 358-360.

Parliment, T. H. 1973. Convenient technique for microhydrogenation. Microchem. J. 18: 613-616.

Patel, P., and G. Pattenden. 1985. Natural polyene α-pyrones. Total synthesis of citreomontanin from *Penicillium pedomontanum*. Tetrahedron Lett. 26: 4789-4792.

Poole, C. F., and S. A. Schuette. 1984. Contemporary Practice of Chromatography. Elsevier, Amsterdam, 708 pp.

Silverstein, R. M., and G. C. Bassler. 1967. Spectrometric Identification of Organic Compounds. John Wiley and Sons, New York, 256 pp.

Smilanick, J. M., L. E. Ehler, and M. C. Birch. 1978. Attraction of Carpophilus sp. to volatile compounds of figs. J. Chem. Ecol. 4: 700-701.

Sonnet, P. E. 1974. cis-Olefins from the Wittig reaction. Org. Prep. Proc. Int. 6: 269-273.

Wicklow, D. T., H. R. Burmeister, P. F. Dowd, and M. G. Smart. 1988. NC-151 progress report for 1987, pp. 30-31. In NC-151, 1987: Annual Progress Reports from Participating Laboratories.

Yates, F. 1940. The recovery of interblock information in balanced incomplete block designs. Ann. Eugen. 10: 317-325.

We claim:

1. A substantially pure compound having the structure:

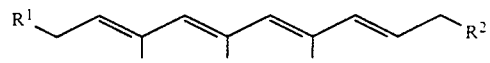

wherein $R^1$ and $R^2$ are independently selected from the group consisting of hydrogen and lower alkyl.

2. A compound as described in claim 1 wherein $R^1$ is hydrogen and $R^2$ is hydrogen.

3. A compound as described in claim 1 wherein $R^1$ is hydrogen and $R^2$ is methyl.

4. An insect attractant composition comprising an inert carrier and a substantially pure compound or a mixture of substantially pure compounds having the structure:

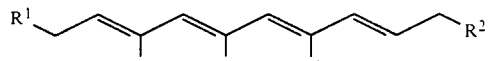

wherein $R^1$ and $R^2$ are independently selected from the group consisting of hydrogen and lower alkyl, said compound or mixture being present in an amount effective as an insect attractant.

5. The composition of claim 4 wherein $R^1$ is hydrogen and $R^2$ is hydrogen.

6. The composition of claim 4 wherein $R^1$ is hydrogen and $R^2$ is methyl.

7. The composition of claim 4 comprising two or more of said compounds.

* * * * *